(12) United States Patent
Rosenberg et al.

(10) Patent No.: US 12,039,851 B2
(45) Date of Patent: Jul. 16, 2024

(54) SYSTEM AND A METHOD FOR SURVEILLING SWIMMERS

(71) Applicant: LIFEGUARD AI, INC., Wilmington, DE (US)

(72) Inventors: Noson Rosenberg, Sfat (IL); Simcha Shore, Eshchar (IL); Ilan Ehrenfeld, Jerusalem (IL)

(73) Assignee: LIFEGUARD AI, INC., Wilmington, DE (US)

( * ) Notice: Subject to any disclaimer, the term of this patent is extended or adjusted under 35 U.S.C. 154(b) by 98 days.

(21) Appl. No.: 17/612,496

(22) PCT Filed: May 20, 2020

(86) PCT No.: PCT/IL2020/050553
§ 371 (c)(1),
(2) Date: Nov. 18, 2021

(87) PCT Pub. No.: WO2020/234880
PCT Pub. Date: Nov. 26, 2020

(65) Prior Publication Data
US 2022/0246017 A1 Aug. 4, 2022

Related U.S. Application Data

(60) Provisional application No. 62/851,680, filed on May 23, 2019.

(51) Int. Cl.
*G08B 23/00* (2006.01)
*A61B 5/021* (2006.01)
(Continued)

(52) U.S. Cl.
CPC ............ *G08B 21/088* (2013.01); *A61B 5/021* (2013.01); *A61B 5/02438* (2013.01);
(Continued)

(58) Field of Classification Search
CPC .. G08B 21/088; G08B 25/009; G08B 29/188; G06V 10/25; G06V 20/52; G06V 40/10; A61B 5/021; A61B 5/02438
(Continued)

(56) References Cited

U.S. PATENT DOCUMENTS

| 11,216,654 | B2 * | 1/2022 | Golan | ........................ G06T 7/73 |
| 2008/0266118 | A1 * | 10/2008 | Pierson | ................ A61B 5/0205 340/573.6 |

(Continued)

FOREIGN PATENT DOCUMENTS

| CN | 108074375 A | 5/2018 |
| CN | 109509330 A | 3/2019 |

OTHER PUBLICATIONS

PCT International Search Report for International Application No. PCT/IL2020/050553, dated Jul. 9, 2020, 3pp.
(Continued)

*Primary Examiner* — Naomi J Small
(74) *Attorney, Agent, or Firm* — The Roy Gross Law Firm, LLC; Roy Gross

(57) ABSTRACT

A swimmer surveillance system configured to detect swimmers in a water body that are in a state of distress, or in a danger of drowning, and provide an alarm signal for prompting assistance to the swimmers in distress or in a danger of drowning, the system including: a processor; at least one swimmer sensor signally connected to the processor, and configured to attach to a swimmer, acquire data relating to an at least one physiological condition of the swimmer, and transmit the data to the processor; at least one image acquiring device signally connected to the processor, and configured to acquire images of the swimmers in the water body, and transmit visual data of the acquired images to the processor; and at least one alarming device signally con-
(Continued)

nected to the processor, and configured to receive a signal from the processor and in response provide an alarm.

11 Claims, 1 Drawing Sheet

(51) Int. Cl.
  *A61B 5/024*   (2006.01)
  *G06V 10/25*   (2022.01)
  *G06V 20/52*   (2022.01)
  *G06V 40/10*   (2022.01)
  *G08B 21/08*   (2006.01)
  *G08B 25/00*   (2006.01)
  *G08B 29/18*   (2006.01)

(52) U.S. Cl.
  CPC .............. *G06V 10/25* (2022.01); *G06V 20/52* (2022.01); *G06V 40/10* (2022.01); *G08B 25/009* (2013.01); *G08B 29/188* (2013.01)

(58) Field of Classification Search
  USPC ...................................................... 340/573.6
  See application file for complete search history.

(56) References Cited

U.S. PATENT DOCUMENTS

| | | | |
|---|---|---|---|
| 2009/0219785 A1* | 9/2009 | Van ''T Klooster | G01S 11/16 |
| | | | 367/134 |
| 2016/0037138 A1* | 2/2016 | Udler | G06V 20/52 |
| | | | 348/143 |
| 2017/0167151 A1* | 6/2017 | Segal | E04H 4/065 |
| 2018/0040223 A1* | 2/2018 | Bodi | G08B 21/18 |
| 2019/0071962 A1* | 3/2019 | Gottlieb | H04B 11/00 |
| 2019/0211576 A1* | 7/2019 | Bella | E04H 4/14 |
| 2020/0023238 A1* | 1/2020 | Firmin | H04N 13/218 |
| 2023/0098667 A1* | 3/2023 | Mekonnen | A61P 35/00 |
| | | | 514/220 |

OTHER PUBLICATIONS

PCT Written Opinion for International Application No. PCT/IL2020/050553, dated Jul. 9, 2020, 5pp.

* cited by examiner

SYSTEM AND A METHOD FOR SURVEILLING SWIMMERS

CROSS-REFERENCE TO RELATED APPLICATION

This application is a National Phase of PCT Patent Application No. PCT/IL2020/050553 having International filing date of May 20, 2020, which claims the benefit of priority of U.S. Provisional Patent Application No. 62/851,680, filed May 23, 2019, the contents of which are all incorporated herein by reference in their entirety.

FIELD

The present subject matter relates to surveillance systems and methods. More particularly, the present subject matter relates to swimmer surveillance systems and methods.

BACKGROUND

Swimmers in water bodies, for example swimming pools, are prone to being in a state of distress, or even in danger of drowning. Therefore, there is a need for systems and methods for surveilling the swimmers that detect swimmers that are in a state of distress, or in a danger of drowning, in order to prevent further harm to the swimmers by alarming life guards or people in the vicinity of the water bodies and prompt them to provide assistance, or even rescue, the swimmers that are in a state of distress, or in a danger of drowning.

Currently available swimmer surveillance systems have some drawbacks. For example, systems that are based on surveillance cameras are not able to surveil swimmers that are hidden, for example by other swimmers, or objects like sea mattresses.

SUMMARY

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

According to one aspect of the present subject matter, there is provided a swimmer surveillance system configured to detect swimmers in a water body that are in a state of distress, or in a danger of drowning, and provide an alarm signal for prompting assistance to the swimmers in distress or in a danger of drowning, the system comprising:
  a processor;
  at least one swimmer sensor signally connected to the processor, and configured to attach to a swimmer, acquire data relating to an at least one physiological condition of the swimmer, and transmit the data to the processor;
  at least one image acquiring device signally connected to the processor, and configured to acquire images of the swimmers in the water body, and transmit visual data of the acquired images to the processor; and
  at least one alarming device signally connected to the processor, and configured to receive a signal from the processor and in response provide an alarm, wherein the processor is configured to receive the data from the at least one swimmer sensor, or from the at least one image acquiring device, or from both the at least one swimmer sensor and the at least one image acquiring device, determine according to the received data whether a swimmer is in a state of distress or in a danger of drowning based on the acquired data, and when determining that a swimmer is in a state of distress or in a danger of drowning—send a signal to the alarming device.

According to one embodiment, the swimmer surveillance system further comprising at least one display signally connected to the processor, and configured to receive data from the processor and display the data.

According to another embodiment, the physiological condition of the swimmer is heartbeat rate, or blood pressure, or level of oxygen in blood.

According to still another embodiment, the swimmer sensor is configured to transmit to the processor a unique identification tag, and the processor is configured to receive the unique identification tag and attribute the unique identification tag to the swimmer sensor that transmitted the unique identification tag.

According to a further embodiment, the at least one swimmer sensor is configured to transmit acoustic signals, and the swimmer surveillance system further comprising at least one relay acoustically connected to the at least one swimmer sensor, and signally connected to the processor, wherein the relay is configured to receive the acoustic signals transmitted from the swimmer sensor, convert the acoustic signals to converted signals, and transmit the converted signals to the processor, and wherein the processor is configured to receive the converted signals.

According to yet a further embodiment, the relay comprising:
  an acoustic receiver acoustically connected to the at least one swimmer sensor;
  a convertor acoustically connected to the acoustic receiver; and
  a transmitter signally connected to the convertor and signally connected to the processor.

According to still a further embodiment, the acoustic receiver is configured to be positioned in the water of the water body, and receive acoustic signals conducted through the water, and the at least one swimmer sensor is configured to transmit acoustic signals to the water of the water body.

According to an additional embodiment, at least one relay is positioned at at least one corner of the water body, or on at least one bank of the water body, or a combination thereof.

According to yet an additional embodiment, the processor is configured to calculate a vector indicating a direction and distance of a swimmer sensor from the relay 2, by analyzing a direction and an amplitude of an acoustic signal received from a swimmer sensor by a relay.

According to still an additional embodiment, the processor is configured to determine a position of the swimmer sensor in the water body by interpolating multiple vectors calculated for the swimmer sensor from multiple relays positioned at different locations aside the water body.

According to another embodiment, the swimmer surveillance system comprises at least one stationary image acquiring device, or at least one mobile image acquiring device, or a combination thereof.

According to yet another embodiment, the processor is configured to detect when a swimmer is in a state of distress, or in a danger of drowning, according to movements of the swimmer that are detected by the at least one image acquiring device.

According to a further embodiment, the processor is configured to determine whether a swimmer is in a state of distress or in a danger of drowning, by
- determining whether a head of the swimmer is above a water surface or below the water surface;
- measuring a time duration in which the head of the swimmer is below the water surface; and
- comparing the time duration in which the head of the swimmer is below the water surface with a predetermined time threshold,
- wherein if the time duration in which the head of the swimmer is below the water surface is longer than the time threshold, then the processor is configured to transmit a signal to the alarming device.

According to still a further embodiment, the processor is configured to determine whether a head of a swimmer is above a water surface or below the water surface, by
- defining a region of interest (ROI) in an image received from the image acquiring device in which a head of a swimmer is present;
- calculating an area ratio between the area of the head and the area of the ROI; and
- comparing the area ratio with a predetermined area ration threshold,
- wherein if the area ratio is lower than the area ratio threshold then the head of the swimmer is below the water surface; and if the area ration is higher than the area ratio threshold then the head of the swimmer is above the water surface.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

DESCRIPTION OF THE PREFERRED EMBODIMENTS

Figure 1:
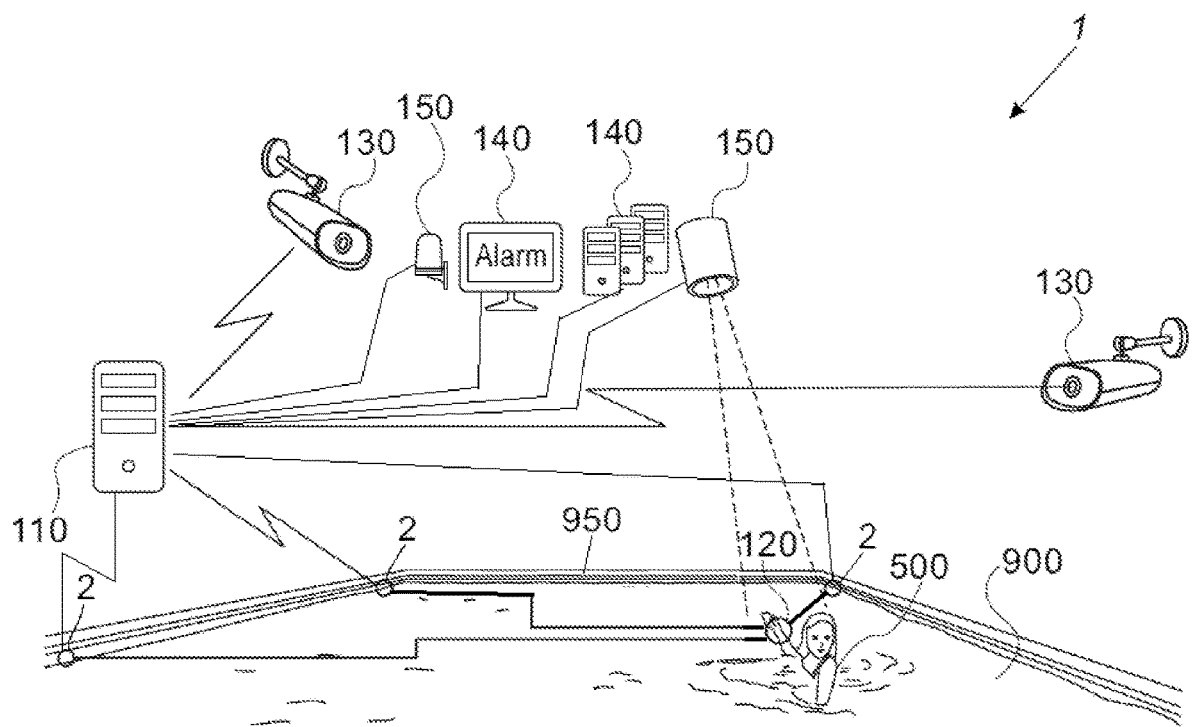
FIG. 1 schematically illustrates, according to an exemplary embodiment, a front perspective view of a swimmer surveillance system.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

The present subject matter provides a system for surveilling swimmers in a water body, for example a swimming pool, in order to detect swimmers that are in a state of distress, or in a danger of drowning, and provide an alarm signal for prompting assistance to the swimmers in distress or in a danger of drowning.

The present subject matter further provides a method for surveilling swimmers in a water body, for example a swimming pool, in order to detect swimmers that are in a state of distress, or in a danger of drowning, and provide an alarm signal for prompting assistance to the swimmers in distress or in a danger of drowning.

Referring now to FIG. 1, schematically illustrating, according to an exemplary embodiment, a front perspective view of a swimmer surveillance system. FIG. 1 illustrates a swimmer surveillance system 1.

The present subject matter provides a swimmer surveillance system 1 configured to detect swimmers 500 in a water body 900 that are in a state of distress, or in a danger of drowning, and provide an alarm signal for prompting assistance to the swimmers 500 in distress or in a danger of drowning, the system comprising:
- a processor 110;
- at least one swimmer sensor 120 signally connected to the processor 110, and configured to attach to a swimmer 500, acquire data relating to an at least one physiological condition of the swimmer 500, and transmit the data to the processor 110;
- at least one image acquiring device 130 signally connected to the processor 110, and configured to acquire images of the swimmers 500 in the water body 900, and transmit visual data of the acquired images to the processor 110; and
- at least one alarming device 150 signally connected to the processor 110, and configured to receive a signal from the processor 110 and in response provide an alarm signal, wherein the processor 110 is configured to receive the data from the at least one swimmer sensor 120, or from the at least one image acquiring device 130, or from both the at least one swimmer sensor 120 and the at least one image acquiring device 130, determine according to the received data whether a swimmer 500 is in a state of distress or in a danger of drowning based on the acquired data, and when determining that a swimmer 500 is in a state of distress or in a danger of drowning—send a signal to the alarming device 150.

According to one embodiment, the water body 900 is a swimming pool.

The swimmer sensor 120 is configured to attach to a body of a swimmer 500. The number of swimmer sensors 120 in the swimmer surveillance system 1 is at least equal to the number of swimmers 500 in the water body 900. The aim is that a swimmer sensor 120 will be attached to each swimmer 500 present in the water body 900. The swimmer sensor 120 can attach to the body of the swimmer 500, for example, but not limited to, as a wrist, as a forehead band, as a sensor attached to a goggle used by the swimmer 500, and the like.

Furthermore, the swimmer sensor 120 can attach to any part of a body of the swimmer 500, for example head, arm, leg, neck, belly and the like.

According to one embodiment, the swimmer sensor 120 is water proof. According to another embodiment, the swimmer sensor 120 is configured to withstand water pressure. This embodiment can allow the swimmer sensor 120 not to be damaged and continue functioning when the swimmer 500 dives in the water body 900. According to another embodiment, the swimmer sensor 120 is configured to withstand water pressure in depths of common water bodies. For example, the swimmer sensor 120 is configured to withstand a water pressure of a water depth of up to substantially 5 meters.

The swimmer sensor 120 is configured to acquire data relating to an at least one physiological condition of the swimmer 500, for example, but not limited to, heartbeat rate, blood pressure, level of oxygen in blood and the like.

The processor 110 is configured to receive data that are transmitted from the at least one swimmer sensor 120, analyze the data received from the at least one swimmer sensor 120, and detect as well as identify various conditions of the at least one swimmer 500 that can be used for determining whether a swimmer 500 is in a state of distress or in danger of drowning. In other words, the processor 110 is configured to identify a state of distress in a swimmer 500 according to the physiological data received from the swimmer sensor 120. Moreover, the processor 110 is configured to distinguish between a state of distress and a state of normal pressure due to controlled exercise, like swimming, diving or playing in the water body 900. It is important to distinguish between the state of distress and the state of normal pressure in order to prevent false alerts, like considering a swimmer 500 is in a state of distress, while actually the swimmer 500 only put some extra effort in swimming and is in a state of normal pressure. One exemplary way to distinguish between a state of distress and a state of normal pressure due to controlled exercise is by monitoring the rate of change in a measured physiological parameter, for example heartbeat rate. During normal controlled exercise the change in the physiological parameter is gradual, while in a state of distress the change in the physiological parameter is very rapid and sudden.

In order to be able to exert the aforementioned analysis and decision whether a swimmer 500 is in a state of distress, or normal pressure simply, according to one embodiment, the processor 110 is further configured to preform machine learning and deep learning. According to another embodiment, the processor 110 comprises at least one algorithm for machine learning and deep learning based on data that are received by the processor 110.

According to an additional embodiment, the processor 110 is configured to use data that received from the at least one swimmer sensor 120 to determine whether a swimmer 500 has a physiological condition or health condition, that may be a potential risk to the swimmer 500, for example a danger of getting a heart attack, an abnormal rise in blood pressure, and the like. According to yet an additional embodiment, based on such a determination, the processor 110 is configured to provide recommendations to a swimmer 500, for example a recommendation to stop exercise and have a rest. These embodiments can be achieved due to the ability of the processor 110 to perform machine learning and deep learning based on data that are received by the processor 110 from the swimmer sensor 120.

According to one embodiment, each swimmer sensor 120 is configured to transmit to the processor 110 a unique identification tag, and the processor 110 is configured to receive the unique identification tag and attribute the unique identification tag to the swimmer sensor 120 that transmitted the unique identification tag. This embodiment can allow identification of each swimmer 500 in the water body 900, given that swimmers 500 do not change the swimmer sensor 120 attached to them, or the swimmer sensor 120 is not detached from the body of the swimmer 500.

According to one embodiment, the at least one swimmer sensor 120 is configured to transmit the data to the processor 110. According to another embodiment, the transmission rate of data from the swimmer sensor 120 is suitable for the processor 110 to get reliable information about the condition of swimmers 500 in the water body 900, and provide an alert rapidly in order to timely assist a swimmer 500 that is in a state of distress or in a danger of drowning. For example, according to one embodiment, data are transmitted from the swimmer sensor every substantially 0.5 seconds. It should be noted that this transmission rate is only exemplary and should not be considered as limiting the scope of the present subject matter.

Some exemplary mechanism for transmitting data from the at least one swimmer sensor 120 to the processor 110 include, but not limited to, radio frequency transmission, acoustic transmission, ultrasonic transmission, and the like. According to a preferred embodiment, the swimmer sensor 120 is configured to transmit acoustic signals to the processor 110, either directly, or indirectly as described hereinafter. According to another preferred embodiment, the swimmer sensor 120 is configured to acoustically transmit signals to a relay 2, and the relay 2 is configured to transmit the signals to the processor 110 preferably electronically, either in a wired manner or wirelessly, as described hereinafter.

Figure 2:
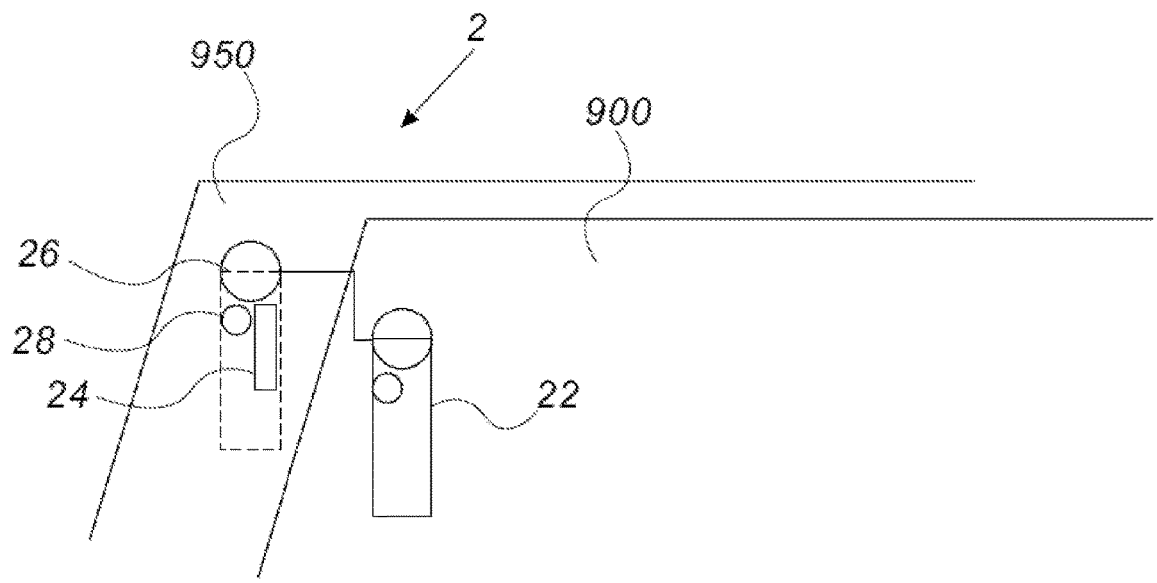
FIG. 2 schematically illustrates, according to an exemplary embodiment, a front perspective view of a relay.

Referring now to FIG. 2, schematically illustrating, according to an exemplary embodiment, a front perspective view of a relay. FIG. 2 illustrates a relay 2, embodiments of which are described hereinafter.

According to one embodiment, the at least one swimmer sensor 120 is configured to transmit acoustic signals, and the swimmer surveillance system 1 further comprises at least one relay 2 acoustically connected to the at least one swimmer sensor 120, and signally connected to the processor 110, wherein the relay 2 is configured to receive the acoustic signals transmitted from the swimmer sensor 120, convert the acoustic signals to converted signals, and transmit the converted signals to the processor 110, and wherein the processor 110 is configured to receive the converted signals.

According to one embodiment, the converted signal is a radio signal, an electronic signal, and the like.

According to one embodiment, the at least one relay 2 is signally connected to the processor 110, either in a wired manner, or wirelessly.

According to one embodiment, the relay 2 comprises:
- an acoustic receiver 22 acoustically connected to the at least one swimmer sensor 120;
- a convertor 24 acoustically connected to the acoustic receiver 22; and
- a transmitter 26 signally connected to the convertor 24 and signally connected to the processor 110.

According to one embodiment, the acoustic receiver 22 is configured to receive acoustic signals from the at least one swimmer sensor 120. An exemplary acoustic receiver 22 is a microphone and the like. According to another embodiment, the acoustic receiver 22 is configured to be positioned in the water of the water body 900, and receive acoustic signals conducted through the water, and the at least one swimmer sensor 120 is configured to transmit acoustic signals to the water of the water body 900.

According to another embodiment, the acoustic receiver 22 is configured to transmit the at least one acoustic signal to the convertor 24.

According to the embodiment, the convertor 24 is configured to receive acoustic signals from the acoustic receiver 22. According to another embodiment, the convertor 24 is configured to convert the acoustic signals to converted signals. Examples of a converted signal include an electrical signal, a radio signal and the like. According to yet another embodiment, the converter 24 is configured to transmit the converted signals to the transmitter 26.

According to one embodiment, the transmitter 26 is configured to receive converted signals from the convertor 24. According to another embodiment, the transmitter 26 is configured to transmit the converted signals to the processor 110. The converted signals can be transmitted from the transmitter 26 to the processor 110 by, for example, but not limited to, wireless transmission, radio transmission, Bluetooth and the like; or wired transmission and the like.

According to one embodiment, the relay 2 can further comprise at least one amplifier configured to amplify signals that are processed by the relay 2. Below are some exemplary embodiments of an amplifier.

According to one embodiment, the relay 2 comprises an acoustic signal amplifier, acoustically connected between the acoustic receiver 22 and the converter 24, and configured to receive acoustic signals from the acoustic receiver 22, amplify the acoustic signals to get amplified acoustic signals, and transmit the amplified acoustic signals to the converter 24.

According to a further embodiment, the relay 2 comprises a converted signal amplifier, signally connected between the converter 24 and the transmitter 26, and configured to receive converted signals from the converter 24, amplify the converted signals to get amplified converted signals, and transmit the amplified converted signals to the transmitter 26.

According to an additional embodiment, the relay 2 comprise an acoustic signal amplifier and a converted signal amplifier.

The at least one relay 2 can be positioned in any position on an edge of the water body 900. According to one embodiment, at least one relay 2 is positioned at at least one corner of the water body 900, or on at least one bank of the water body 900, or a combination thereof.

According to one embodiment, the swimmer surveillance system 1 comprises at least one relay 2. According to another embodiment, the swimmer surveillance system 1 comprises a multiplicity of relays 2. According to yet another embodiment, the swimmer surveillance system 1 comprises at least three relays 2.

According to one embodiment, the processor 110 is configured to determine a position in the water body 900 of a swimmer 500 according to signals received from a swimmer sensor 120 attached to a swimmer 500. This can be achieved, for example, by analyzing signals received by the relays 2 and transmitted to the processor 110.

According to one embodiment, the processor 110 is configured to calculate a vector indicating a direction and distance of a swimmer sensor 120 from the relay 2, by analyzing a direction and an amplitude of an acoustic signal received from a swimmer sensor 120 by a relay 2.

According to another embodiment, the processor 110 is configured to determine a position of the swimmer sensor 120 in the water body 900 by interpolating multiple vectors calculated for the swimmer sensor 120 from multiple relays 2 positioned at different locations aside the water body 900. A reliable determination of the position of the swimmer sensor 120 can be achieved by interpolating at least three vectors calculated for at least three relays 2 positioned at different locations aside the water body 900. Thus, according to a preferred embodiment, the swimmers surveillance system 1 comprises at least three relays 2 positioned at different locations aside the water body 900.

As can be seen in FIG. 2, the relay 2 is installed on a bank 950 of the water body 900. According to one embodiment, the acoustic receiver 22 is positioned inside the water, and the transmitter 26 is positioned outside the water.

According to one embodiment, the relay 2 can further comprise a power source 28 configured to supply power for the operation of components of the relay 2, for example, but not limited to, a battery, a rechargeable battery, a photovoltaic cell, and the like.

According to one embodiment, the at least one image acquiring device 130 is configured to acquire images of swimmers 500 that are in the water body 900, for example, but not limited to, a device configured to acquire still images, a device configured to acquire video images, a device configured to acquire still images and video images, and the like. According to another embodiment, the at least one image acquiring device 130 is configured to transmit data relating to the acquired images to the processor 110.

According to one embodiment, the at least one image acquiring device 130 is configured to cover the entire area of the water body 900. In other words, the at least one image acquiring device 130 is configured to provide to the processor 110 images that cover the entire area of the water body 900. This embodiment is important because it is necessary for the swimmers surveillance system 1 to surveil any swimmer 500 that is present in any location in the water body 900, and therefore there is a need of an at least one image that cover the entire water body 900.

According to one embodiment, the swimmer surveillance system 1 comprises at least one stationary image acquiring device 130, or at least one mobile image acquiring device 130, or a combination thereof. The stationary image acquiring device 130 is permanently positioned in one place, in a manner that allows the image acquiring device 130 to acquire images of at least part of the water body 900. The mobile image acquiring device 130 is configured to move from one place to another, while acquiring images of the water body 900, or while not acquiring images of the water body 900. The at least one image acquiring device 130 can be rendered mobile by, for example, at least one rail on which the at least one image acquiring device 130 is configured to slide, wheels attached to the image acquiring device 130 that allow movement of the image acquiring device 130 in the vicinity of the water body 900, at least one moving arm to which the at least one image acquiring device 130 is attached and the like.

According to one embodiment, the at least one image acquiring device 130 is configured to continuously acquire images of the water body 900 and swimmers 500 in the water body 900.

The processor 110 is a computing device. According to one embodiment, the processor 110 is a single computing unit that can be positioned anywhere, for example in the vicinity of the water body 900, or in a remote place. Another example is that the processor 110 is a cloud, and the mechanisms of transmitting and receiving data to and from the processor 110 are similar to the mechanisms of transmitting and receiving data to and from clouds.

According to one embodiment, the processor 110 is physically divided to multiple components. For example, part of the processor 110 can be in a cloud and part of the processor 110 can be in a computing device in the vicinity of the water body 900. Another example is that parts of the processor 110 can be physically present in at least one of the components of the swimmer surveillance system 1, for example as part of the at least one swimmer sensor 120, or as part of the at least one image acquiring device 130, or as part of the at least one relay 2, or any combination thereof.

According to one embodiment, the processor 110 comprises at least one software that administers the activities of the swimmer surveillance system 1, as described herein, for example monitoring swimmers 500 in the water body 900, issuing alarms when necessary, administering drowning events and the like. According to another embodiment, the processor 110 is configured to run algorithms of the various activities performed by the swimmer surveillance system 1.

According to one embodiment, the processor 110 is configured to receive data from the at least one swimmer sensor 120. According to another embodiment, the processor 110 is configured to receive data from the at least one image acquiring device 130. According to yet another embodiment, the processor 110 is configured to receive data from the at least one swimmer sensor 120 and the at least one image acquiring device 130. According to a further embodiment, the processor 110 is configured to analyze the data that were received and determine whether a swimmer 500 is in a state of distress or in a danger of drowning. According to yet a further embodiment, the processor 110 is configured to perform a deep learning process during the analysis of the data that were received and during the determination whether a swimmer 500 is in a state of distress or in a danger of drowning. According to an additional embodiment, the processor 110 is configured to transmit a signal to the alarming device 150, and in response the alarming device 150 is configured to provide an alarm for prompting assistance to the swimmer 500 in distress or in a danger of drowning.

According to one embodiment, the processor 110 is configured to determine a time duration in which a head is under a water surface for each swimmer 500 present in the water body 900, compare the time duration to a predetermined time threshold, and transmit a signal to the alarming device 150 when the time duration is longer than the time threshold. As a result, the alarming device 150 is configured to provide an alarm in order to prompt assistance to the swimmer 500 that his head is under the water surface for a time duration that is longer than the time threshold.

According to one embodiment, the processor 110 is configured to detect when a swimmer 500 is in a state of distress, or in a danger of drowning. According to another embodiment, the processor 110 is configured to detect when a swimmer 500 is in a state of distress, or in a danger of drowning, according to movements of the swimmer 500 that are detected by the at least one image acquiring device 130. According to yet another embodiment, the processor 110 is configured to detect when a swimmer 500 is in a state of distress, or in a danger of drowning, according to data relating to an at least one physiological condition of the swimmer 500 that are acquired by the at least one swimmer sensor 120.

According to one embodiment, the processor 110 is configured to combine the surveillance with the at least one swimmer sensor 120 with the surveillance with the at least one image acquiring device 130. In other words, the processor 110 is configured to combine data received from the at least one swimmer sensor 120 and the at least one image acquiring device 130 in order to determine whether a swimmer 500 is in a state of distress or in a danger of drowning. For example, when according to signals acquired from the at least one swimmer sensor 120, the processor 110 determines that there is a swimmer 500 in the water body 900 that is in a state of distress, or in a danger of drowning, the processor 110 is configured to focus an image on the swimmer 500, or on a suspected region where the swimmer 500 is presumed to be, with the at least one image acquiring device 130, for example by determining the position of the swimmer 500 as described above. Furthermore, the processor 110 is configured to tag the swimmer, or his presumed location, for example on a display showing images acquired by the at least one image acquiring device 130. In addition, the processor 110 is further configured to determine the state of the tagged swimmer 500, or the state of swimmers 500 present in the tagged presumed location, for example by analyzing movements of the swimmers 500. Furthermore, the processor 110 is also configured to provide an alarm relating to the swimmer 500 that is tagged. In addition, the processor 110 is configured to follow the swimmer 500 until he is being assisted or rescued. This exemplary combination of swimmer sensors 120 and image acquiring devices 130 increases the reliability and accuracy of the detection of swimmers that are in a state of distress, or in a danger of drowning.

The combination of data acquired by the at least one swimmer sensor 120 and the at least one image acquiring device 130 is advantageous over the usage of only at least one swimmer sensor 120, or at least one image acquiring device 130. For example, there are cases in which a swimmer 500 is not detected by the at least one image acquiring device 130, for example when the swimmer 500 is concealed by another swimmer 500, or by an object, like a sea mattress. In a system comprising only at least one image acquiring device 130, the concealed swimmer 500 can be in a state of distress, or in a danger of drowning, without the system being able to detect the concealed swimmer's 500 situation. The combination of the at least one swimmer sensor 120 and an at least image acquiring device 130, of the present subject matter, overcomes this problem since the swimmer sensor 120 can provide data about the position of the swimmer 500 in the water body 900, and his physiological condition, also when he is concealed to the at least one image acquiring device 130.

Other examples involve uncertainty about the identification of a swimmer 500 being visually seen by the at least one image acquiring device 130. For example, in cases when multiple swimmers 500 are very close one to the other, a swimmer 500 that dived into the water in one location and got back to the water surface in another location, a swimmer 500 that dived into the water in a certain location while another swimmer jumped into the water at the same location, and the like. For such cases, the combination of an at least one swimmer sensor 120 and an at least one image acquiring device 130 is advantageous. For example, the processor 110 is configured, according to one embodiment, to combine the unique identification tags of the at least one swimmer sensor 120 to the images acquired by the at least one image acquiring device 130. As a result, every swimmer 500 seen in the images is tagged and has a unique identification, thus overcoming the aforementioned uncertainties about the identification of swimmers 500 seen in the images.

Another example of the advantage of the combination of the at least one swimmer sensor 120 and the at least one image acquiring device 130, is in situations when a swimmer 500 is diving in the water body 900 under the water surface. A system comprising only at least one image acquiring device 130 can provide in this case an alarm because the head of the diving swimmer 500 is under the water surface for a time duration that is longer than a predetermined time threshold. On the other hand, the swimmer surveillance system 1 of the present subject matter can detect that the physiological condition of the diving swimmer 500 is normal, namely the diving swimmer 500 is not in a state of distress, or in a danger of drowning.

Yet, another example of the advantage of the combination of the at least one swimmer sensor 120 and the at least one image acquiring device 130, is in situations when for example the at least one swimmer sensor 120 stops functioning, for example due to detachment of the swimmer sensor 120 from the body of the swimmer 500; or malfunction of the swimmer sensor 120; or emptying out of a power source, like a battery, of the swimmer sensor 120; or malfunction of the connection of the swimmer sensor 120 with the processor 110. In such cases, when the system comprises only at least one swimmer sensor 120, there is a danger that a swimmer 500 is in a state of distress, or in a danger of drowning, but the system would not detect this situation, because the swimmer sensor 120 does not function. On the other hand, the swimmer surveillance system 1 of the present subject matter allows surveillance of swimmers 500 by the at least one image acquiring device 130 also when there is malfunction of the at least one swimmer sensor 120. Furthermore, when for example a swimmer sensor 120 is detached from s swimmer 500, the image acquiring device 130 can detect it and provide a notice relating the swimmer 500 from which the swimmer sensor 120 is detached.

Still, another example of the advantage of the combination of the at least one swimmer sensor 120 and the at least one image acquiring device 130, is in situations when for example individuals that have no permission to enter into the water body 900 do enter the water body 900. The swimmer surveillance system 1 of the present subject matter is configured to detect incidents of non-permitted individuals entering the water body 900. For example, a toddler is not permitted to enter into the water body 900 without supervision by an adult. Nevertheless, the toddler enters the water body 900 without being noticed. Since the toddler is not supposed to enter the water body 900, a swimmer sensor 120 is not attached to the toddler. In such a case, the at least one image acquiring device 130 transmits to the processor 110 images of the toddler entering the water body 900. However, no signal of a swimmer sensor 120 is received by the processor 110. In such a case, the processor 110 is configured to transmit a signal to the alarming device 150, indicating that a non-permitted individual entered the water body 900. Thus, such an embodiment can prevent tragic events of, for example, drowning of toddlers after entering a water body 900 without being noticed.

According to one embodiment, the swimmer surveillance system 1 further comprises at least one display 140 signally connected to the processor 110, and configured to receive data from the processor 110 and display the data. Exemplary displays 140 include a monitor, a screen of a smartphone and the like. According to a further embodiment, the at least one display 140 is configured to display any type of data received from the processor 110, for example still images and video images acquired by the at least one image acquiring device 130; written texts, for example written alerts, data about swimmers like their identifications, physiological data and like. According to one embodiment, the data are displayed automatically, for example images of the water body 900, its vicinity and swimmers 500, are displayed automatically. Another example is alerts that are displayed automatically when there is a need to issue an alert. According to another embodiment, the data are displayed by request. For example, when a user desires to see physiological data of a certain swimmer 500, he may request this data and the data is displayed.

As described above, the swimmer surveillance system 1 comprises an alarming device 150, configured to receive signals from the processor 110 and in response provide an alarm. Some exemplary alarming devices 150 include: the display 140 of the swimmer surveillance system 1 that is configured to display text messages or images of alarm; a noise alarming device, like a bell, a siren, a horn and the like; a light source, like a lamp, at least one monitor placed for example in the vicinity of the water body 900, or in a control room, or in a building in the vicinity of the water body 900; at least one mobile computer, for example smartphones, tablets, smart watches and the like; a projector illuminating a swimmer 500 that was detected as being in a state of distress or in a danger of drowning, and the like.

According to one embodiment, the swimmer surveillance system 1 is configured to track at least one swimmer 500 from a time he enters into water body 900 until the time the at least one swimmer 500 gets out of the water body 900. In other words, the swimmer surveillance system 1 is configured to track at least one swimmer 500 during a period of time in which the at least one swimmer 500 is in the water body 900. According to another embodiment, the swimmer surveillance system 1 is configured to track individuals that are in the vicinity of the water body 900. According to yet another embodiment, the swimmer surveillance system 1 is configured to track swimmers that are in the water body 900 and individuals that are in the vicinity of the water body 900.

According to another embodiment, the swimmer surveillance system 1 is configured to track a head of an at least one swimmer 500 during the period of time in which the at least one swimmer 500 is in the water body 900. According to yet another embodiment, the swimmer surveillance system 1 is configured to determine whether a head of a swimmer 500 is above the water surface or below the water surface by analyzing images of the water body 900. This embodiment is important because it allows the swimmer surveillance system 1 to determine whether a swimmer 500 is in a danger of drowning. The determining whether a head of a swimmer 500 is above the water surface or below the water surface by analyzing images of the water body 900 can be achieved, for example, by methods involving algorithms for computer vision. Following are some exemplary methods for such an analysis.

Thus, according to one embodiment, the processor 110 is configured to determine whether a swimmer 500 is in a state of distress or in a danger of drowning, by determining whether a head of the swimmer 500 is above a water surface or below the water surface; measuring a time duration in which the head of the swimmer 500 is below the water surface; and comparing the time duration in which the head of the swimmer 500 is below the water surface with a predetermined time threshold, wherein if the time duration in which the head of the swimmer 500 is below the water surface is longer than the time threshold, then the processor 110 is configured to transmit a signal to the alarming device 150.

According to one embodiment, the processor 110 is configured to determine whether a head of a swimmer 500 is above a water surface or below the water surface, by defining a region of interest (ROI) in an image received from the image acquiring device 130 in which a head of a swimmer 500 is present, calculating an area ratio between the area of the head and the area of the ROI, and comparing the area ratio with a predetermined area ration threshold, wherein if the area ratio is lower than the area ratio threshold then the head of the swimmer 500 is below the water surface; and if the area ration is higher than the area ratio threshold then the head of the swimmer 500 is above the water surface.

Another exemplary method for determining whether a head of a swimmer 500 is above the water surface or below the water surface comprises a process of deep learning. An exemplary deep learning process can comprise learning to determine whether a nose, or a mouth, or a nose and a mouth of a swimmer 500 is above the water surface or underneath the water surface.

According to a further embodiment, the swimmer surveillance system 1 is configured to handle cases when the head of swimmer 500 is lost during tracking.

The present subject matter further provides a method for detecting swimmers in a state of distress or in a danger for drowning, and alerting when such incidents occur. Various embodiments of the method are described above in relation to the swimmer surveillance system 1 and its components that are configured to perform the various embodiments of the method.

According to one embodiment, the swimmer surveillance system 1 is configured to operate automatically, without any intervention by a human user. According to another embodiment, the swimmer surveillance system 1 is configured to operate under supervision by a human user, namely supervised operation of the swimmer surveillance system 1, for example in order to determine whether the swimmer surveillance system 1 operates properly and for example does not miss incidences in which a swimmer 500 is in a state of distress or in a danger of drowning. Another purpose for supervised operation of the swimmer surveillance system 1 can be for quality control in order to catch and fix malfunctions of the swimmer surveillance system 1.

During supervised operation of the swimmer surveillance system 1, a human supervisor watches data displayed on a monitor 140, for example images acquired by the at least one image acquiring device 130. When the human supervisor detects a swimmer 500 that is in a state of distress or in a danger of drowning, he presses for example an alert button that sends an alert signal to a computing device, for example a smartphone of a lifeguard or an owner of the water body 900. This way, the automatic operation of the swimmer surveillance system 1, that should transmit a signal to the alarming device 150 as well, can be compared to the operation of the human supervisor.

According to one embodiment, an automatic alert signal is generated as soon as possible after detecting a swimmer 500 that is in a state of distress or in a danger of drowning, in other words, the automatic alert signal is generated instantaneously upon detection of a swimmer 500 that is in a state of distress or in a danger of drowning. According to another embodiment, the automatic alert signal, in addition to be exerted by the alarming device 150, it is also exerted by the computing device of the lifeguard, or owner. According to yet another embodiment, the automatic alert signal can take control of the volume settings of the computing device, and for example, exert an alarm in a very high sound intensity, for example at the highest sound intensity of the computing device. According to still another embodiment, the automatic alert signal can take control of a display of the computing device, for example a screen of a smartphone, and display a visual alert, like an alert message, on the display. According to a further embodiment, images that were acquired before, or during, or after, the time of the event, or a combination thereof, can be displayed as well on the display of the computing device.

In addition, according to one embodiment, the processor 110 is further configured to maintain a database of alert events that occurred, as well as data that were received by the processor 110 during these alert events, and during the entire time of operation of the swimmer surveillance system 1. In addition, the database can maintain snapshots, for example of a few seconds, that were acquired by the at least one image acquiring device 130, before, during, and after an alert event. The database can be accessible by any authorized entity, for example an owner of the water body 900.

According to another embodiment, multiple swimmer surveillance systems 1, each operating on a different water body 900 can be linked to a central where a human supervisor could supervise their operation. This can be achieved by using multiple displays, each displaying data from a different swimmer surveillance system 1, or by displaying data from multiple swimmer surveillance systems 1 on one display, and using algorithms that prioritize display of data according to events occurring in the surveilled water bodies 900. For example, when a swimmer 500 in a state of distress is detected in a certain water body 900, data from the swimmer surveillance system 1 that operates in the water body 900 are prioritized and displayed on the display. In addition to display of data, prioritization can be also on alarming signals that are also transmitted to the central.

According to one embodiment, a central database can also be connected to multiple processors 110 from multiple swimmer surveillance systems 1. The central database is configured to store data received from the multiple processors 110, and can be accessible to authorized entities, for example an owner of multiple water bodies 900, the processors 110 of which are connected to the central database.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A swimmer surveillance system configured to detect swimmers in a water body that are in a state of distress, or in a danger of drowning, and provide an alarm signal for prompting assistance to the swimmers in distress or in a danger of drowning, the system comprising:
 a processor;
 at least one swimmer sensor signally connected to the processor, and configured to attach to a swimmer, acquire data relating to an at least one physiological condition of the swimmer, and transmit the data to the processor;
 at least one image acquiring device signally connected to the processor, and configured to acquire images of the swimmers in the water body, and transmit visual data of the acquired images to the processor; and at least one alarming device signally connected to the processor, and configured to receive a signal from the processor and in response provide an alarm, wherein the processor is configured to receive the data from both the at least one swimmer sensor, or and from the at least one image acquiring device, or from both the at least one swimmer sensor and the at least one acquired imaging device, wherein the processor determines according to the received data whether a swimmer is in a state of distress or in a danger of drowning based on the acquired data, and when determining that a swimmer is in a state of distress or in a danger of drowning the processor sends a signal to the alarming device, wherein the processor is configured to determine whether a swimmer is in a state of distress or in a danger of drowning, by determining whether a head of the swimmer is above a water surface or below the water surface;

measuring a time duration in which the head of the swimmer is below the water surface; and comparing the time duration in which the head of the swimmer is below the water surface with a predetermined time threshold, wherein if the time duration in which the head of the swimmer is below the water surface is longer than the time threshold, then the processor is configured to transmit a signal to the alarming device, wherein the processor is configured to determine whether a head of a swimmer is above a water surface or below the water surface, by defining a region of interest (ROI) in an image received from the image acquiring device in which a head of a swimmer is present;

calculating an area ratio between the area of the head and the area of the ROI; and comparing the area ratio with a predetermined area ratio threshold, wherein if the area ratio is lower than the area ratio threshold then the head of the swimmer is below the water surf ace; and if the area ratio is higher than the area ratio threshold then the head of the swimmer is above the water surface.

2. The swimmer surveillance system of claim 1, further comprising at least one display signally connected to the processor, and configured to receive data from the processor and display the data.

3. The swimmer surveillance system of claim 1, wherein the physiological condition of the swimmer is heartbeat rate, or blood pressure, or level of oxygen in blood.

4. The swimmer surveillance system of claim 1, wherein the swimmer sensor is configured to transmit to the processor a unique identification tag, and the processor is configured to receive the unique identification tag and attribute the unique identification tag to the swimmer sensor that transmitted the unique identification tag.

5. The swimmer surveillance system of claim 4, wherein the processor is configured to calculate a vector indicating a direction and distance of a swimmer sensor from the relay, by analyzing a direction and an amplitude of an acoustic signal received from a swimmer sensor by a relay.

6. The swimmer surveillance system of claim 5, wherein the processor is configured to determine a position of the swimmer sensor in the water body by interpolating multiple vectors calculated for the swimmer sensor from multiple relays positioned at different locations aside the water body.

7. The swimmer surveillance system of claim 1, wherein the swimmer surveillance system comprises at least one stationary image acquiring device, or at least one mobile image acquiring device, or a combination thereof.

8. The swimmer surveillance system of claim 1, wherein the processor is configured to detect when a swimmer is in a state of distress, or in a danger of drowning, according to movements of the swimmer that are detected by the at least one image acquiring device.

9. The swimmer surveillance system of claim 1, wherein the at least one image acquiring device is configured to cover the entire area of the water body.

10. The swimmer surveillance system of claim 1, wherein the at swimmer surveillance system is configured to operate automatically without any human intervention.

11. The swimmer surveillance system of claim 1, wherein the at least one image acquiring device is rendered mobile by at least one rail on which the at least one image acquiring device is configured to slide, wheels attached to the image acquiring device that allow movement of the image acquiring device in the vicinity of the water body.

* * * * *